(12) United States Patent
Black

(10) Patent No.: US 9,757,170 B2
(45) Date of Patent: *Sep. 12, 2017

(54) SECURING FASTENERS

(71) Applicant: GLOBUS MEDICAL, INC., Audubon, PA (US)

(72) Inventor: Michael E. Black, Swarthmore, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/270,199

(22) Filed: Sep. 20, 2016

(65) Prior Publication Data

US 2017/0014168 A1    Jan. 19, 2017

Related U.S. Application Data

(63) Continuation of application No. 14/829,777, filed on Aug. 19, 2015, now Pat. No. 9,468,482, which is a continuation of application No. 14/252,313, filed on Apr. 14, 2014, now Pat. No. 9,138,271, which is a continuation of application No. 13/352,464, filed on Jan. 18, 2012, now Pat. No. 8,734,495.

(51) Int. Cl.
*A61B 17/80* (2006.01)
*A61B 17/86* (2006.01)
*A61B 17/70* (2006.01)

(52) U.S. Cl.
CPC ...... *A61B 17/8047* (2013.01); *A61B 17/7059* (2013.01); *A61B 17/8605* (2013.01); *A61B 17/8685* (2013.01)

(58) Field of Classification Search
CPC ................... A61B 17/8047; A61B 17/8605
See application file for complete search history.

(56) References Cited

U.S. PATENT DOCUMENTS

| 7,001,389 B1 | 2/2006 | Navarro et al. |
| 2006/0122604 A1 | 6/2006 | Gorhan et al. |

FOREIGN PATENT DOCUMENTS

| JP | 2003214416 A | 7/2003 |
| JP | 2003254310 A | 9/2003 |
| JP | 2008522722 A | 7/2008 |

*Primary Examiner* — Andrew Yang

(57) ABSTRACT

A polyaxial fastener is secured within an implant with a retaining ring. The ring is assembled onto a circumferential groove formed in the fastener head. The groove and ring are positionable, when the fastener is installed into an implant, at a wide portion of the mating polyaxial aperture in the implant. The ring is compressible into the groove to form a narrowed diameter, which is passable into a narrow diameter of the aperture, near an entrance to the aperture. The ring is released to expand and increase an overall diameter of the head and ring assembly, thereby rending the assembly too wide to pass by the narrow entrance to the aperture, thereby securing the assembly within the implant.

17 Claims, 4 Drawing Sheets

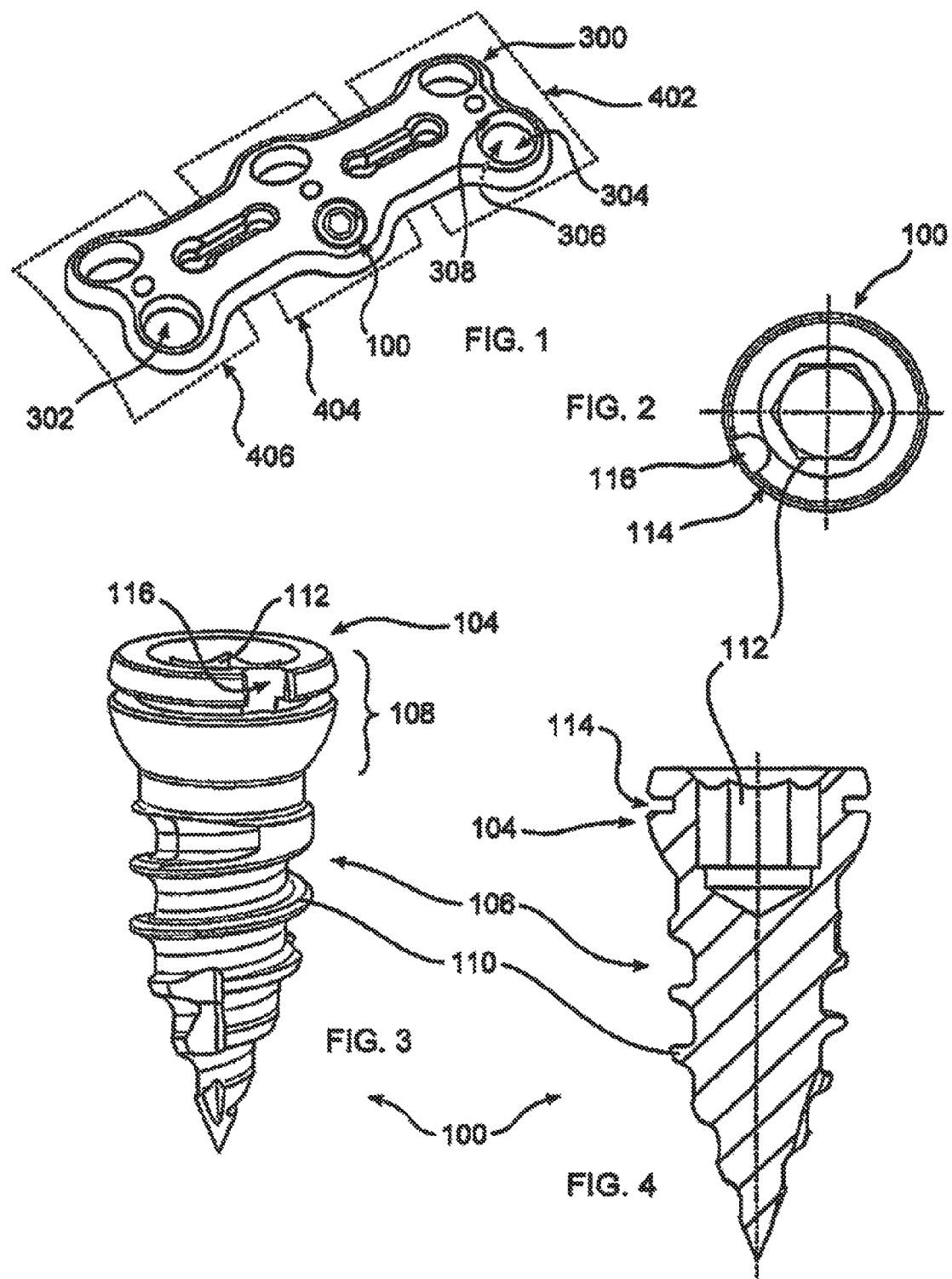

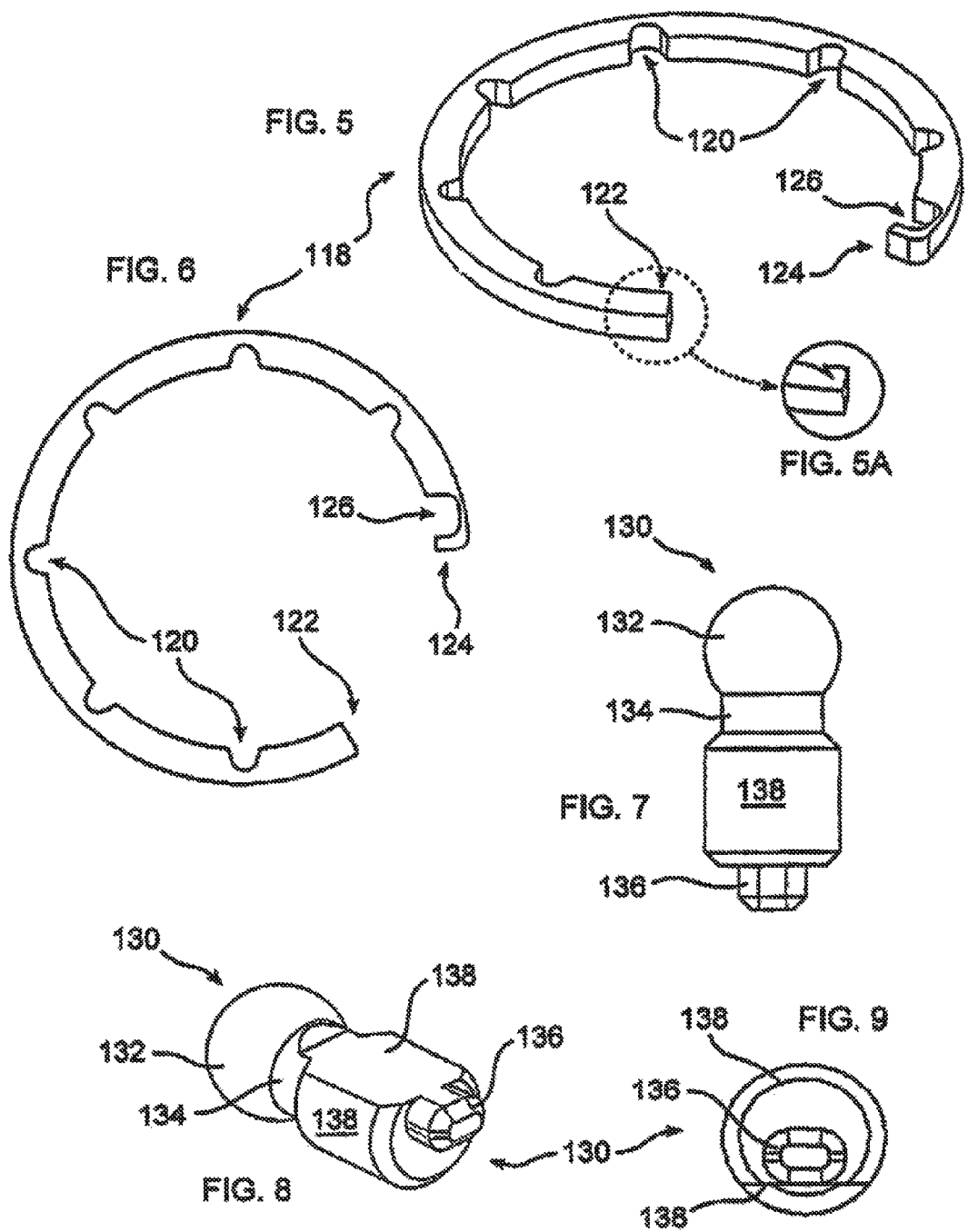

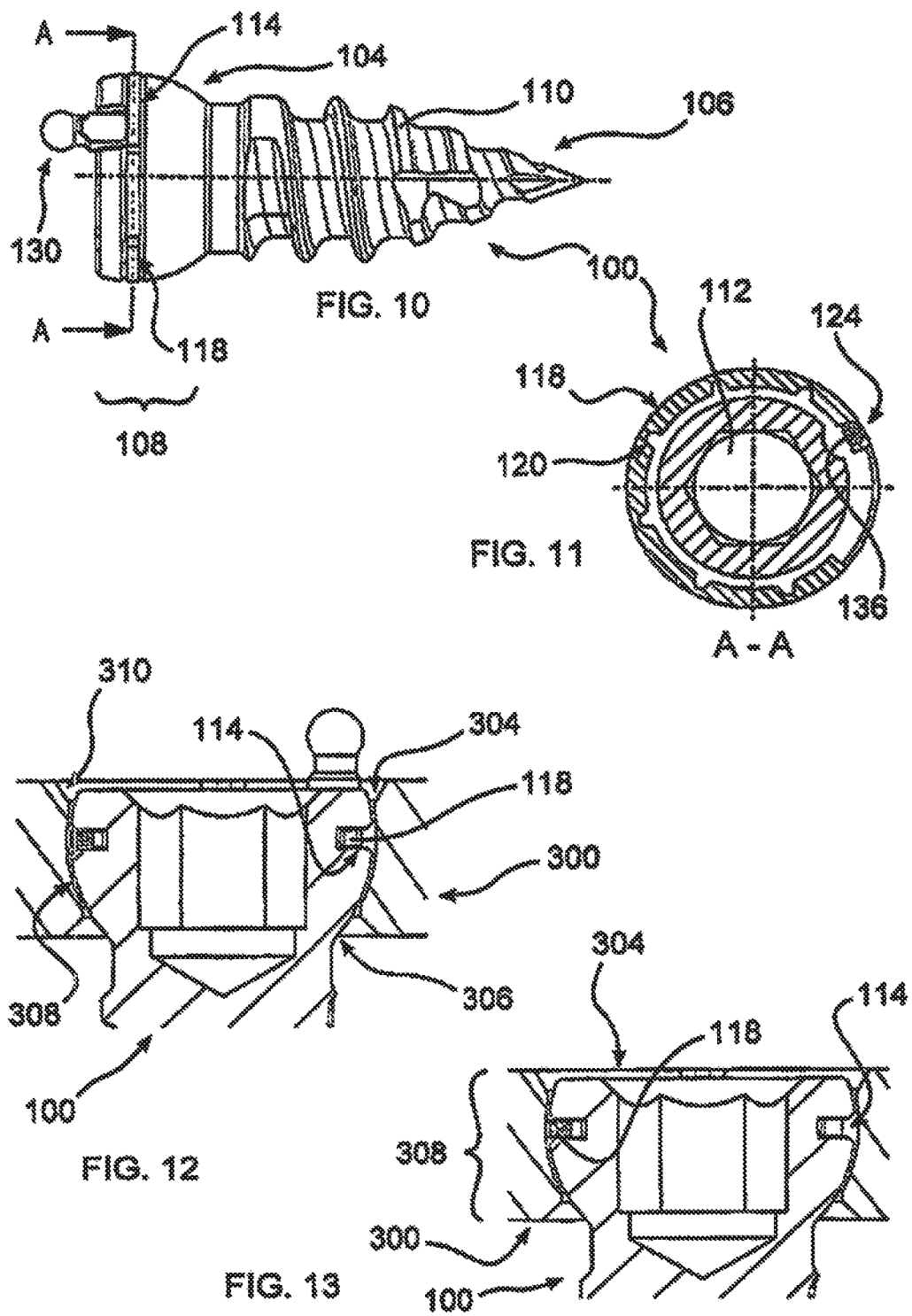

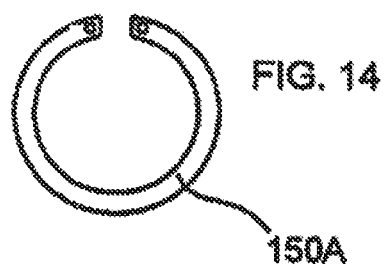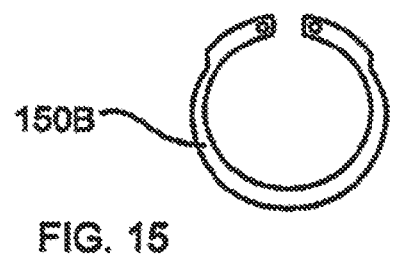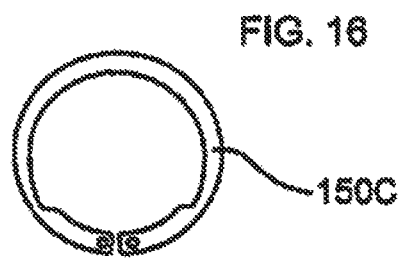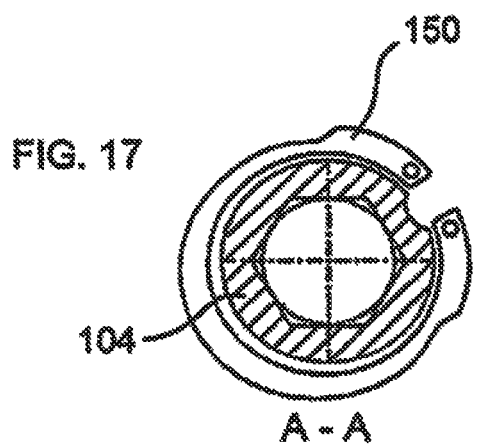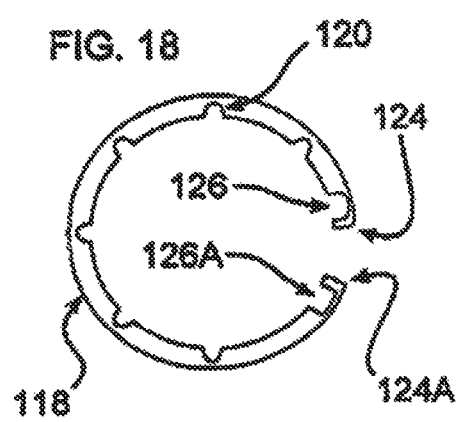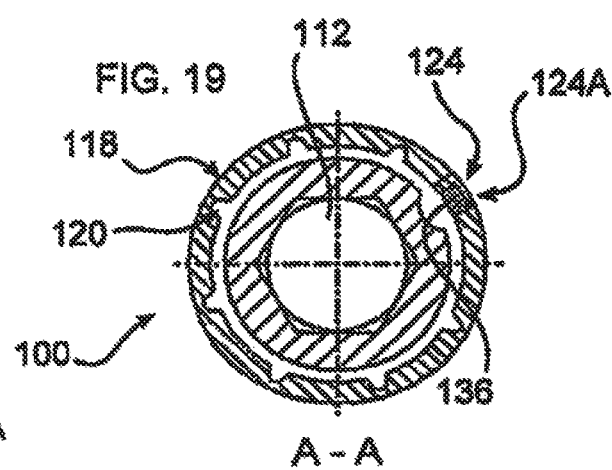

SECURING FASTENERS

CROSS-REFERENCE TO RELATED APPLICATIONS

This application is a continuation of U.S. patent application Ser. No. 14/829,777, filed Aug. 19, 2015, which is a continuation of U.S. patent application Ser. No. 14/252,313, filed on Apr. 14, 2014, now issued as U.S. Pat. No. 9,138,271, which is a continuation of U.S. patent application Ser. No. 13/352,464, filed Jan. 18, 2012, now issued as U.S. Pat. No. 8,734,495, filed on Jan. 18, 2012, which are each incorporated herein by reference in their entirety.

FIELD OF THE INVENTION

The invention relates to securing fasteners within the body, and more particularly to securing a fastener head within an aperture in an implant.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

The cervical spine has presented challenges for doctors, partially due to the small size of the vertebrae and the spacing between adjacent vertebrae. Typically, weaknesses in the cervical spine, for example, are corrected by using devices that fuse one or more vertebrae together. Common devices involve plate systems that align and maintain adjacent cervical vertebrae in a desired position, with a desired spacing.

These devices, commonly referred to as bone fixation plating systems, typically include one or more plates and screws for aligning and holding vertebrae in a fixed position with respect to one another. Initial devices used stainless steel plates and screws. In order to remain fixed in place, the screws were required to pass completely through the vertebrae and into the spinal canal. These devices caused many complications and involved significant risks. To allow a screw to pass, drilling and then tapping of the vertebrae was required. In the process, instruments came within close proximity of the spinal cord, which required extreme care on the part of the surgeon.

In addition to the risks of surgically applying bone fixation plates, other complications arose. Commonly, these problems involve loosening and failure of the hardware. Two common failures are the breakage of the plates, and the backing out of the screws into soft tissues of the patient's body. The backing out of the screws is typically a result of the screws failure to achieve a sufficient purchase in the bone, although the stripping of the screws has also been known to cause this problem. Regardless of the cause of the hardware failures, a surgeon must repair or replace the broken parts, which requires undesirable invasive procedures.

SUMMARY OF THE INVENTION

In accordance with the disclosure, a fastener is insertable within an implant in a body, where the implant has an aperture through which the fastener may be inserted, the aperture including a curved inner profile defining a larger dimension and a smaller dimension, the fastener comprising: an elongated body; a head connected to the body and defining a curved profile mateable with the curved inner profile of the implant, the head further including a circumferential groove disposable proximate the larger dimension of the curved inner profile of the implant when the head is mated with the implant; and an open ring sized to be positionable partly within the circumferential groove to extend from the circumferential groove to thereby increase a widest dimension of the head, the ring formed with a resilient material, the ring resiliently expandable from a first compressed configuration having a first dimension to a second relaxed configuration having a second dimension, the second dimension larger than the first dimension, the head passable into the aperture when the ring is assembled into the groove and the ring is in the first compressed configuration, and the head not passable out of the aperture when the ring is resiliently expanded to the second configuration, due to the ring interfering in the second configuration with the smaller dimension of the curved inner profile.

In embodiments, the ring further includes a first end and a second end, the first end fixable within the groove, the second end moveable to change the ring from the first configuration to the second configuration; the ring further includes a first end and a second end, the first end fixed within the circumferential groove, and the second end moveable to change a shape of the ring from the first compressed configuration to the second relaxed configuration, the second end including a notch releasably engageable to maintain the ring in the first compressed configuration; a pin is removably connectable with the head and insertable into the notch to engage the notch to maintain the ring in the first compressed configuration, or removed from the notch to disengage the notch and enable the ring to resiliently expand to the second dimension.

In other embodiments, the fastener head is a polyaxial fastener head; the aperture is formed in an implant selected from the group consisting of bone plate, bone spacer, and prosthetic device; the fastener head further includes an access port through which an object may be inserted to maintain the ring in the first compressed configuration; the ring forming two ends, at least one of the ends forming a notch, the fastener further including a pin engageable with the head and the notch to maintain the ring in the compressed configuration when the pin is engaged with the head and the notch; the pin further including a pin head engageable with a tool to insert or remove the pin from the notch.

In yet further embodiments, the ring further includes moveable first end second ends, the first and second ends moveable towards each other to form the first configuration of the ring, and releasable to move away from each other to form the second configuration of the ring; and the ring forming first and second ends, the first end fastened within the groove by a method selected from welding, brazing, adhesive, interference fit, and mating hook.

Further in accordance with the disclosure, a fastener is insertable within an implant in a body, the implant having an aperture through which the fastener may be inserted, the aperture including a polyaxial curved inner profile defining a first diameter proximate an entrance to the aperture, and a second larger diameter further within the aperture, the fastener comprising: an elongated body; a polyaxial head connected to the body and defining a curved profile mateable with the curved inner profile of the implant, the head further including a circumferential groove disposable proximate the larger diameter of the curved inner profile of the implant when the head is mated with the implant; an open ring forming first and second ends, the ring sized to be positionable partly within the circumferential groove to extend from the circumferential groove to thereby increase a widest diameter of the head, the ring formed with a resilient material, the ring resiliently expandable from a first compressed configuration having a first dimension to a second relaxed configuration having a second dimension, the second dimension larger than the first dimension, the head passable into the aperture past the first diameter when the ring is assembled into the groove and the ring is in the first compressed configuration, and the head not passable back out of the aperture when the ring is resiliently expanded to the second configuration, due to the ring and assembled ring interfering in the second configuration with the smaller diameter of the curved inner profile, the first ring end fixed within the groove, the second ring end moveable to change the ring between the first and second configurations.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 depicts an implant including an installed fastener of the disclosure;

FIG. 2 depicts a top view of the fastener of FIG. 1;

FIG. 3 depicts a perspective view of the fastener of FIG. 1;

FIG. 4 depicts a section of the fastener of FIG. 1, taken through the longitudinal center of the fastener;

FIG. 5 depicts a perspective view of a retaining ring in accordance with the disclosure;

FIG. 5A depicts an alternative hooked embodiment of the ring of FIG. 5;

FIG. 6 depicts a top view of the ring of FIG. 5;

FIG. 7 depicts a pin in accordance with the disclosure;

FIG. 8 depicts a perspective view of the pin of FIG. 7;

FIG. 9 depicts a bottom view of the pin of FIG. 7;

FIG. 10 depicts an assembly of the fastener of FIG. 1 with the retaining ring of FIG. 5 and pin of FIG. 7;

FIG. 11 depicts a section of the assembly of FIG. 10;

FIG. 12 depicts the assembly of FIG. 10, installed within an implant, in a compressed configuration;

FIG. 13 depicts the assembly of FIG. 12, having the pin removed, the ring in a relaxed configuration, the assembly secured within the implant;

FIGS. 14-16 depicts retaining rings usable to secure the fastener of FIG. 1, in accordance with the disclosure;

FIG. 17 depicts a cross section of the fastener of FIG. 1, assembled with the retaining ring of FIG. 15;

FIG. 18 depicts an alternative retaining ring in accordance with the disclosure, including two moveable ends each having an engagement notch; and FIG. 19 depicts a cross section of the fastener of FIG. 1, assembled with the retaining ring of FIG. 18.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

Referring now to FIG. 1, a fastener 100 of the disclosure is connected to an implant 300 within a patient's body 400 (not shown), by being passed through an implant aperture 302. In the example shown in FIG. 1, implant 300 is joining three portions of body tissue 402, 404, 406, schematically represented as dashed outlines. Body tissue may be bony or soft tissue, and may be a single bone which is strengthened or aligned until healed, or may be multiple bones, for example vertebrae, which are maintained in relative spaced alignment by implant 300. While in the example shown in FIG. 1, implant 300 is a plate, it should be understood that implant 300 may be any object placed into the body for a therapeutic purpose, including for example a body tissue replacement or prosthetic, an instrument or tool, or an autograft, allograft, or xenograft. An example of a stabilizing plate may be found in commonly assigned U.S. Pat. No. 7,963,981, to Binder, et al. While a plate is shown, the disclosure contemplates any implant capable of including an aperture 302 into which fastener 100 may be inserted, including bone spacers, for example an intervertebral spacer, and a prosthetic device, for example an articulating joint surface replacement, or a joint stabilizer, including for example a rod holder.

Additionally referring to FIGS. 12 and 13, implant 300, in accordance with the disclosure includes one or more implant apertures 302 each having an entry 304 that is wider than an exit 306. A tapering or curved profile 308 is defined between entry 304 and exit 306.

With reference to FIGS. 2-4, fastener 100 includes a fastener head 104 having a width wider than exit 306, but which may pass, in a first configuration, through entry 304, as explained further below. Fastener head 104 is advantageously formed with an outer tapering or curved profile 108 that is complementary to inner curved profile 308 of aperture 302. In this manner, fastener extension 106 may be passed through exit 306, and outer and inner curved profiles 108, 308 may be positioned in mating conformity. Provided exit 306 is wider than a width of fastener extension 106, fastener 100 may be swiveled within aperture 302 while maintaining a substantial extent of mutual contact between outer and inner curved profiles 108, 308. Either or both of curved profiles 108, 308 may be provided with a roughened or textured surface to promote maintaining a particular conforming configuration once fastener 100 is tightened. As such, aperture 302 and fastener head 104 form a polyaxial mating surface, wherein fastener 100 may be secured at any of a wide range of angles with respect to implant 300. In one embodiment, fastener 100 forms a polyaxial screw.

Fastener 100 includes threads 110 operative to retain fastener 100 in a desired position. While threads 110 are illustrated, it should be understood that fastener 100 may advantageously include, in accordance with the disclosure, an extension of any known or hereinafter developed type, including as examples circumferential rings, barbs, expanding elements, pivotable elements, cammed elements, tapered threads, self tapping threads, and machine threads. Additionally included is a tool engaging surface 112 which may be internally disposed, as illustrated, or which may be externally formed as an extension of head 104. In the example shown, tool engaging surface is a hex socket; however, any known or hereinafter developed tool engagement may advantageously be used in accordance with the disclosure.

A circumferential groove 114 extends at least partially around head 104, exposed by an access port 116. Groove 114 is sized and dimensioned to receive a retaining ring 118, illustrated in FIGS. 5-6. As explained more fully below, retaining ring 118, when disposed within groove 114 in an expanded configuration, functions to increase a dimension of fastener head 104. When the assembled retaining ring 118 and head 104 are disposed within aperture 302, the assembly 118, 104 is too large to pass out of aperture 302, and fastener 100 is thereby secured within implant 300.

With further reference to FIGS. 5 and 6, retaining ring 118 is formed to have a first, relaxed configuration having a resting diameter, and a second, compressed configuration having a reduced diameter with respect to the relaxed configuration. One or more weakened, narrowed, or more flexible portions 120 formed along an interior periphery of ring 118 facilitate an over-expansion to a dimension greater than the relaxed configuration, for assembly of ring 118 onto fastener head 104, or a contraction from the relaxed to the compressed configuration, without damage or excessive distortion to retaining ring 118. Retaining ring 118 is formed from, or includes, a resilient material, whereby ring 118 expands from the compressed configuration to the relaxed configuration due to this resiliency.

Retaining ring 118 further includes a fixed ring end 122 and a movable ring end 124, which become closer together in the compressed configuration. Fixed ring end 122 may be tethered or affixed within groove 114 by any known means, including welding, brazing, or adhesive. Alternatively, fixed end 122 may be have a larger dimension than a remainder of ring 118, whereby an interference fit is formed with groove 114. In another embodiment, shown in FIG. 5A, fixed ring end 122 may be formed with a hook, mateable with a projection within groove 114 (not shown). In yet another embodiment, retaining ring is machined from the material of fastener head 104.

When fixed ring end 122 is affixed within groove 114, ring 118 may be compressed or relaxed by controlling a position of moveable ring end 124. In one embodiment of the disclosure, ring 118 is placed within groove 114, and is squeezed or coiled inwards about fastener 104 into the compressed configuration by applying pressure to different portions of ring 118. In such configuration, an engagement notch 126 may be aligned with access port 116 of fastener head 104. Once aligned, retaining pin 130 may be inserted through access port 116 and engagement notch 126, to thereby retain ring 118 in the compressed configuration. The assembled fastener 100, ring 118, and pin 130, shown in FIGS. 10-12, may then be fastened to implant 300.

Once fastener head 104 is seated within aperture 302, for example after having been driven into body tissue, pin 130 may be removed by grasping pin head 132 with a tool, for example forceps, or a forked instrument (not shown) operable to engage pin neck 134. Once pin 130 is removed, moveable ring end 124 is free to move in a direction away from fixed ring end 122, and ring 118 is may then expand to the relaxed configuration, as shown in FIG. 13. As the assembled fastener head 104 and ring 118 are disposed within aperture 302, ring 118 expands so that portions of ring 118 become closer to, or engages with, curved profile 308 of aperture 302.

Curved profile 308 forms a progressively smaller diameter towards entry 304. The diameter of fastener head 104 and assembled compressed ring 118 is sufficiently small to pass through entry 304, or is further compressible to pass through entry 304. However, assembled diameter of fastener head 104 and relaxed ring 118 is greater than the narrow diameter proximate entry 304, and therefore when ring 118 is in the relaxed configuration, the assembled fastener head 104 and ring 118 cannot pass back through entry 304, and fastener 100 is thus prevented from separating from implant 300, for example by a backing-out of threads of a threaded fastener 100. It is accordingly advantageous for groove 114 to be formed upon fastener head 104 to correspond to a widest diameter of aperture 302.

As may be seen in FIGS. 7-9, pin 130 may be provided with a cam 136 operative to contact engagement notch 126 to retain ring 118 in the compressed configuration. Pin 130 may further be provided with a curved profile 138 mateable with a surface of fastener head 104, whereby pin 130 may be rotated to either release or contact engagement notch 126. A flattened profile 140 is advantageously provided to avoid interference with aperture 302 during installation of fastener 100 into implant 300. Engagement notch is sized and dimensioned to admit a portion of pin 130, for example cam 136, when pin 130 is assembled onto fastener 100.

In another embodiment, curved profile 308 may be provided with a ramped profile 310 at entry 304, whereby ring 118 may engage ramped profile 310 as fastener 100 is inserted into aperture 302. During engagement, ring 118 may be urged into the compressed configuration by engagement with ramped profile 310, and fastener 100 and assembled ring 118 may thereby form a sufficiently small diameter to pass into aperture 302. As curved profile 308 widens, ring 118 resiliently expands to form a wider diameter, thereby preventing undesired exit of fastener 100 from aperture 302. A bevel (not shown) on a lower ramp engaging surface of ring 118 may advantageously be provided, independent of, or cooperative with ramped profile 310, to facilitate compression of ring 118 during insertion of fastener 100.

With reference to FIGS. 14-17, in a further embodiment, retaining ring 150, shown in various forms 150A-150C, in FIGS. 14-16, has the form of an internal retaining ring or snap ring with apertures for engagement by retaining ring pliers. Retaining ring 150 is inserted into groove 114, and engages curved profile 308 in the manner described for retaining ring 118. Fastener head 104 and or implant 300 may advantageously be provided with removed material in order to admit access to retaining ring pliers.

In accordance with the disclosure, the extent of interference, or cling, between ring 118 or 150 and groove 114, does not prevent ring 118, 150 from returning to a relaxed configuration when not engaged by pin 130 or retaining ring pliers.

With reference to FIGS. 18-19, in accordance with a further embodiment of the disclosure, retaining ring 118 may be provided with two moveable ring ends, including moveable ring end 124A, which is provided with an engagement notch 126A. In this embodiment, engagement notches 126, 126A are overlapped, and pin 130 is positioned within the overlapped notches to maintain ring 118 in a compressed configuration until fastener head 104 is positioned within aperture 302.

All components of fastener 100, including ring 118, 150, pin 130, and implant 300 are advantageously formed from biocompatible materials of suitable strength and wear resistance to perform an intended therapeutic function within the body. Examples of such materials include, but are not limited to, polymers, for example ultra high molecular weight polyethylene or polyoxymethylene copolymer, metals, for example titanium or nitinol, natural materials, bone, autograft, allograft, or xenograft tissue, or composite materials.

Ring 118 may be removed by an instrument (not shown) which is shaped to enter access port 116 and pull engagement notch 126 towards alignment with access port 116, whereby pin 130 or other object may be inserted to prevent uncoiling or relaxing of ring 118. Alternatively, fastener 100 may be pressed against tapered profile 308 while rotated, to coil ring 118 to form the compressed configuration. Ring 150 may be removed with retaining ring pliers.

In accordance with the foregoing, the disclosure provides a device and method for retaining a fastener within an implant. For example, when using certain implants, specifically anterior cervical plates, the utilization of a bone screw locking mechanism of the disclosure provides screw retention that greatly increased the safety of the implanted device. Medical practitioners may have much greater certainty that an implanted device and fastener are locked together. The locking mechanism including fastener 100 and ring 118, 150 of the disclosure provides a visual and tactile confirmation that the screw is locked to the plate. Visible confirmations include the absence of pin 130, as well as the presence of ring 118, 150 occupying the free space between fastener head 104 and curved profile 308, as may be observed through access port 116. An audible and or tactile confirmation is provided when pin 130 is removed, as ring 118 snaps against curved profile 308, or as retaining pliers release retainer 150.

To use fastener 100, retaining ring 118 is assembled into groove 114 in head 104, for example by resiliently bending ring 118, possibly using a tool which engages ring ends 122, 124. Ring 118 is compressed by applying pressure to the ring, possibly using a tool, and pin 130 is assembled into head 104 to pass through retaining ring engagement notch 126 to secure moveable ring end 124. An implant 300 is positioned at a desired location with respect to body tissue 400. Fastener extension 106 is passed into aperture 302, passing through aperture entry 304 and contacting body tissue at aperture exit 306. For threaded fasteners, fastener 100 is rotated, for example through a tool engaged with tool engaging surface 112, or by pushing a barbed or toggling fastener, or by any other means appropriate to the type of fastener extension 106 used. For the retaining rings of FIGS. 14-17, retaining ring pliers may be used to maintain a compressed configuration of ring 118. For ramped or beveled embodiments, insertion force of fastener 100 may be sufficient to compress ring 118 into groove 114 at aperture entry 304. When fastener 100 is seated, outer curved profile 108 of head 104 will be positioned in mating contact with inner curved profile 308 of aperture 302. Where pin 130 is used, pin 130 is removed once head 104 is seated within aperture 302, thereby releasing ring 118 to resiliently expand against aperture inner curved profile 308, to secure head 104 from backing out of a position within aperture 302.

To remove fastener 100, a tool may be passed through fastener access port 116 to draw engagement notch 126 into alignment with access port 116, whereby pin 130 may be reassembled onto head 104 to maintain a compressed configuration of ring 118. Fastener 100 may then be withdrawn using a tool or other means appropriate to the type of fastener extension 106 employed. Retaining ring pliers may be employed for the embodiments of FIGS. 14-17. It should be understood that other embodiments of retaining rings 118 may be provided with apertures similar to those of FIGS. 14-17, whereby retaining ring pliers may be used to compress ring 118. In other embodiments, a sufficient force of unscrewing or withdrawing may be applied operative to break ring 118, particularly for thin, non-metallic, or polymeric retaining rings. Once retaining ring is compressed or broken, fastener 100 may be withdrawn in a like manner as inserted.

In another embodiment, fastener 100 is not connected to body tissue, but connects portions of implant 300. Otherwise, use is correspondingly similar to the foregoing description.

Additional fasteners, and or longer fasteners, have been employed in the prior art to reduce a likelihood that a fastened implant will come loose. The instant disclosure provides an alternative to these methods, because a medical practitioner can be certain that the fasteners implanted will not back out of engagement with the implant. A drawback to longer screws is that long screws do not allow for sufficient movement of the vertebrae to accommodate the compression of a bone graft, because the purchase of the screws is too great. Thus, the vertebrae cannot move and are unable to adjust to the compression of the bone graft. The instant disclosure provides a way to reliably use shorter screws which permit sufficient, but not excessive, movement of the vertebrae to maintain compression of a bone graft. A drawback to additional fasteners is increased time in surgery, increased cost in materials, and further trauma to the body. The instant disclosure therefore provides for reducing these drawbacks.

The instant disclosure further provides an alternative to placing a second plate or structure on top of a fastener. This avoids the additional bulk and undesirable interference with and irritation to overlying body tissue, as well as the additional installation time required for assembly during surgery. Examples of undesirable consequence of a bulky implant include dysphasia, and wear to neighboring tissue, which may include the aorta, or vena cava.

The instant disclosure further prevents backing out of fasteners due to tiny vibrations, or micromotions, through the resilient and continual engagement of ring 115, 150 with curved profile 308.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A spinal implantation system comprising:
   a plate comprising a first aperture for receiving a first fastener and a second aperture for receiving a second fastener;
   a first fastener extendable through the first aperture, wherein the first fastener comprises a head portion and an extension portion, wherein the head portion comprises a groove; and
   a retaining ring received in the groove of the first fastener, wherein the retaining ring is configured to have a compressed configuration and a relaxed configuration, wherein when the retaining ring is in the compressed configuration the first fastener is insertable into the first aperture, wherein when the retaining ring is in the relaxed configuration the first fastener is prevented from back out of the first aperture, wherein the retaining ring has a pair of ends such that the retaining ring does not form a complete diameter, wherein the pair of ends of the retaining ring comprises a fixed ring end and a movable ring end.

2. The spinal implantation system of claim 1, wherein the movable ring end comprises an engagement notch.

3. The spinal implantation system of claim 2, wherein the head portion of the first fastener comprises an access port.

4. The spinal implantation system of claim 3, wherein in the compressed configuration the engagement notch of the retaining ring and the access portion of the first fastener are aligned.

5. The spinal implantation system of claim 4, further comprising a retaining pin, wherein the retaining pin is received in the access port and the engagement notch to retain the ring in the compressed configuration.

6. The spinal implantation system of claim 1, further comprising a retaining pin for maintaining the retaining ring in the compressed configuration.

7. The spinal implantation system of claim 6, wherein the retaining pin comprises a cam member.

8. A spinal implantation system comprising:
   a plate comprising a first aperture for receiving a first fastener and a second aperture for receiving a second fastener;
   a first fastener extendable through the first aperture, wherein the first fastener comprises a head portion and an extension portion, wherein the head portion comprises a groove;
   a retaining ring received in the groove of the first fastener, wherein the retaining ring is configured to have a compressed configuration and a relaxed configuration, wherein when the retaining ring is in the compressed configuration the first fastener is insertable into the first aperture, wherein when the retaining ring is in the relaxed configuration the first fastener is prevented from back out of the first aperture; and
   a retaining pin for maintaining the retaining ring in the compressed configuration.

9. The spinal implantation system of claim 8, wherein the retaining ring comprises a fixed ring end and a movable ring end.

10. The spinal implantation system of claim 9, wherein the movable ring end comprises an engagement notch.

11. The spinal implantation system of claim 10, wherein the head portion of the first fastener comprises an access port.

12. The spinal implantation system of claim 11, wherein in the compressed configuration the engagement notch of the retaining ring and the access portion of the first fastener are aligned.

13. The spinal implantation system of claim 12, wherein the retaining pin is received in the access port and the engagement notch to retain the ring in the compressed configuration.

14. The spinal implantation system of claim 8, wherein the plate comprises third and fourth apertures.

15. The spinal implantation system of claim 8, wherein the retaining pin comprises a cam member.

16. The spinal implantation system of claim 8, wherein the retaining ring has a pair of ends such that the retaining ring does not form a complete diameter.

17. The spinal implantation system of claim 16, wherein the pair of ends of the retaining ring comprises a fixed ring end and a movable ring end.

* * * * *